(12) United States Patent
Kawamura

(10) Patent No.: US 6,713,490 B2
(45) Date of Patent: Mar. 30, 2004

(54) 3,4-DIHYDROQUINOLIN-2(1H)-ONE COMPOUNDS AS NR2B RECEPTOR ANTAGONISTS

(75) Inventor: Mitsuhiro Kawamura, Aichi (JP)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/413,029

(22) Filed: Apr. 14, 2003

(65) Prior Publication Data
US 2003/0216430 A1 Nov. 20, 2003

Related U.S. Application Data

(60) Provisional application No. 60/375,939, filed on Apr. 26, 2002.

(51) Int. Cl.$^7$ ................... A61K 31/4709; C07D 401/06
(52) U.S. Cl. ...................... 514/312; 546/158; 546/157; 546/153
(58) Field of Search ........................ 514/312; 546/158, 546/157, 153

(56) References Cited

U.S. PATENT DOCUMENTS 4,902,695 A  2/1990  Ornstein

FOREIGN PATENT DOCUMENTS

| WO | WO 91/17156 | 11/1991 | |
| WO | WO 94/10166 | 5/1994 | |
| WO | 94/10166 | * 5/1994 | ................. 514/312 |
| WO | WO 02/16321 | 2/2002 | |

OTHER PUBLICATIONS

PCT Search Report, PCT/USIB03/01556.
Klockgether T. et al., "Toward an Understanding of the Role of Glutamate in Experimental Parkinsonism: Agonist–Sensitive Sites in the Basal Ganglia", Ann Neurol. 1993; 34: p. 585–593.
McLachlan, R., "Suppression of Spreading Depression of Leão in Neocortex by an N–Methyl–D–Aspartate Receptor Antagonist", Can. J. Neurol. Sci, 19 (4), p. 487, 1992.
Francis P.T., et al., "Cortical Pyramidal Neurone Loss May Cause Glutamatergic Hypoactivity and Cognitive Impairment in Alzheimer's Disease: Investigative and Therapeutic Perspectives", J. Neurochem., 1993; 60(5): p. 1589–1604.
Lipton S.et al., "Excitatory amino acids as a final common pathway for neurologic disorders", New Eng. J. Med., 1994; 330(9): p. 613–622.
Lehmann, J., "The NMDA Receptor", Drugs of the Future 14, No. 11, p. 1059 (1989).
Andreassen, O.A., et al., "Inhibition by memantine of the development of persistent oral dyskinesias induced by long–term haloperidol treatment of rats", Br J Pharmacol, 1996; 119: p. 751–7.
Hardin–Pouzet, II., et al., Glutamate Metabolism is Down–Regulated in Astrocytes During Experimental Allergic Encephalomyelitis, Glia, 1997; 20: p. 79–85.
Wallstrom, E., et al., "Memantine abrogates neurological deficits, but not CNS inflammation, in Lewis rat experimental autoimmune encephalomyelitis", J. Neurol. Sci., 1996; 137: p. 89–96.
Mao, J., et al., "Mechanism of hyperalgesia and morphine tolerance: A current view of their possible interactions", Pain 1995; 62: p. 259–74.
Trujillo, K.A., et al., Inhibition of opiate tolerance by non–competitive N–methyl–D–aspartate receptor antagonists, Brain Res 1994; 633: p. 178–88.
Trujillo, K.A., et al., Inhibition of morphine tolerance and dependence by the NMDA receptor antagonist MK–801, Science 1991, 251: 85–7.
Carey, R. J., et al., "The NMDA Receptor and Cocaine: Evidence that MK–801 Can Induce Behavioral Sensitization Effects", Pharmacol Biochem Behav, 1995; 51: p. 901–8.
Karler, R., et al., Excitatory amino acids and the actions of cocaine, Brain Res 1992, 582: p. 143–6.
Hölter, S. M., et al., "Evidence for alcohol anti–craving properties of memantine", Eur J. Pharmacol, 1996; 314: R1–R2.
Trujillo, K.A., et al., Inhibition of morphine tolerance and dependence by the NMDA receptor antagonist MK–801, Science 1991, 251: 85–7.

* cited by examiner

Primary Examiner—Charanjit S. Aulakh
(74) Attorney, Agent, or Firm—Charles W. Ashbrook; David R. Kurlandsky

(57) ABSTRACT

This invention provides a compound which is (R)-6-[2-[4-(3-fluorophenyl)-4-hydroxy-1-piperidinyl]-1-hydroxyethyl]-3,4-dihydro-2(1H)-quinolinone or a pharmaceutically acceptable ester of such compound, or a pharmaceutically acceptable salt thereof. The compound is useful for the treatment of disease conditions caused by overactivation of NMDA NR2B receptor such of pain, stroke, traumatic brain injury, Parkinson's disease, Alzheimer's disease, depression, anxiety, migraine, or the like in mammalian, especially humans. This invention also provides a pharmaceutical composition comprising the above compound.

6 Claims, No Drawings

3,4-DIHYDROQUINOLIN-2(1H)-ONE COMPOUNDS AS NR2B RECEPTOR ANTAGONISTS

This application claims the benefit of U.S. Provisional Application Ser. No. 60/375,939 filed Apr. 26, 2002.

TECHNICAL FIELD

This invention relates to novel 3,4-dihydroquinolin-2(1H)-one compounds. These compounds are useful as antagonists of NMDA (N-methyl-D-aspartate) NR2B receptor, and are thus useful for the treatment of pain, stroke, traumatic brain injury, Parkinson's disease, Alzheimer's disease, depression, anxiety, migraine, or the like in mammalian, especially humans. The present invention also relates to a pharmaceutical composition comprising the above compounds.

BACKGROUND ART

Glutamate plays dual role in the central nervous system (CNS) as essential amino acid and the principal excitatory neurotransmitters. There are at least four classes of receptors, specifically N-methyl-aspartate (NMDA), 2-amino-3-(methyl-3-hydroxyisoxazol-4-yl)propionic acid (AMPA), kainate and metabotropic. There is considerable preclinical evidence that hyperalgesia and allodynia following peripheral tissue or nerve injury is not only due to an increase in the sensitivity of primary afferent nociceptors at the site of injury but also depends on NMDA receptor-mediated central changes in synaptic excitability. In humans, NMDA receptor antagonists have also been found to decrease both pain perception and sensitization. Also, overactivation of NMDA receptor is a key event for triggering neuronal cell death under pathological conditions of acute and chronic forms of neurodegeneration. However, while NMDA receptor inhibition has therapeutic utility in the treatment of pain and neurodegenerative diseases, there are significant liabilities to many available NMDA receptor antagonists that can cause potentially serious side effects. NMDA subunits are differentially distributed in the CNS. Especially, NR2B is believed to be restricted to the forebrain and laminas I and II of the dosal horn. The more discrete distribution of NR2B subunit in the CNS may support a reduced side-effect profile of agents that act selectively at this site.

For example, NMDA NR2B selective antagonists may have clinical utility for the treatment of neuropathic and other pain conditions in human with a reduced side-effect profile than existing NMDA antagonists (S. Boyce, et al., Neuropharmacology, 38, pp.611–623 (1999)).

International Publication Number WO 91/17156 and WO94/10166 discloses a variety of 3,4-dihydroquinolin-2(1H)-one compounds. Especially, a compound represented by the following formula is disclosed in WO 94/10166:

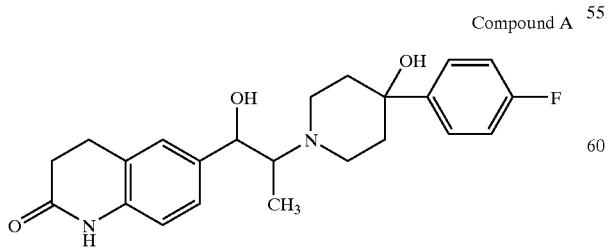

Compound A

However, the known compounds have potential to prolong the QT-interval due to their potent inhibitory activity at HERG (human ether-a-go-go related gene) potassium channel. QT prolongation is known to have a potential liability to produce fatal cardiac arrhythmias of Torsades de Pointes (TdP). The ability to prolong the cardiac action potential duration was identified as being due to an action at the HERG potassium channel. For example, drugs withdrawn from the market due to QT prolongation, such as Cisapride and Terfenadine, are known to be potent HERG potassium channel blocker (Expert Opinion of Pharmacotherapy; 2, pp947–973, 2000). Therefore, it would be desirable if there were provided a novel NMDA NR2B selective antagonist with analgesic activity by systemic administration and with reduced inhibitory activity at HERG potassium channel.

BRIEF DISCLOSURE OF THE INVENTION

It has now surprisingly been found that a specific sub-set of compounds broadly covered by WO 91/17156 are NMDA NR2B selective antagonists with superior activity and with reduced inhibitory activity at HERG channel. Inhibitory activity at HERG channel was estimated from affinity for HERG type potassium channel was investigated by checking [$^3$H]dofetilide binding, which can predict inhibitory activity at HERG channel (Eur. J. Pharmacol., 430, pp147–148, 2001).

The present invention provides a compound of the following formula (I):

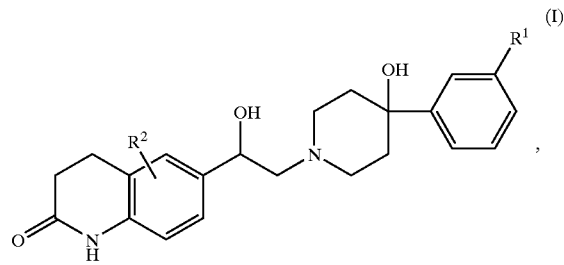

wherein $R^1$ is fluoro, chloro, bromo, $C_{1-3}$ alkyl or $C_{1-3}$ alkoxy; and $R^2$ is hydrogen, fluoro, chloro, bromo, $C_{1-3}$ alkyl or $C_{1-3}$ alkoxy or a pharmaceutically acceptable ester of such compound, or a pharmaceutically acceptable salt thereof.

According to formula (I), $R^1$ is preferably fluoro, $C_{1-3}$ alkyl, e.g. methyl or $C_{1-3}$ alkoxy, e.g. methoxy. $R^1$ is most preferably fluoro.

According to formula (I), $R^2$ is preferably hydrogen.

According to formula (I), the asymmetric centre —C(OH)— is preferably in the (R) configuration.

A suitable sub-group of compounds of formula (I) are those represented by formula (I-a)

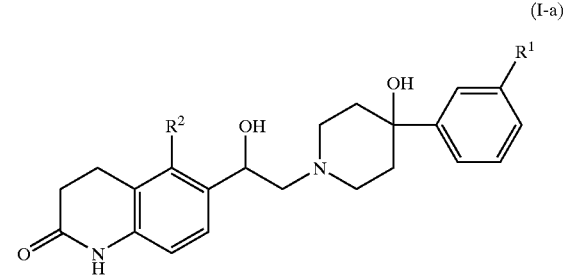

wherein $R^1$ is fluoro or methoxy; and $R^2$ is hydrogen or fluoro,

As used herein, the term "$C_{1-3}$ alkyl" includes methyl, ethyl, n-propyl, iso-propyl.

As used herein, the term "$C_{1-3}$ alkoxy" includes methoxy, ethoxy, n-propoxy, iso-propoxy.

Suitable compounds according to the present invention are selected from:

6-[1-hydroxy-2-[4-hydroxy-4-(3-methoxyphenyl)-1-piperidinyl]ethyl]-3,4-dihydroquinolin-2(1H)-one;

5-fluoro-6-[1-hydroxy-2-[4-hydroxy-4-(3-methoxyphenyl)-1-piperidinyl]ethyl]-3,4-dihydroquinolin-2(1H)-one; and 6-[1-hydroxy-2-[4-hydroxy-4-(3-methylphenyl)piperidin-1-yl]ethyl]-3,4-dihydroquinolin-2(1H)-one;

or a pharmaceutically acceptable ester of such compound, or a pharmaceutically acceptable salt thereof.

A preferred individual compound of this invention is:

(R)-6-[2-[4-(3-fluorophenyl)-4-hydroxy-1-piperidinyl]-1-hydroxyethyl]-3,4-dihydroquinolin-2(1H)-one or a pharmaceutically acceptable ester of such compound, or a pharmaceutically acceptable salt thereof.

The 3,4-dihydroquinolin-2(1H)-one compounds of this invention have an antagonistic action towards NMDA NR2B receptor subtype selectively and are thus useful in therapeutics, particularly for the treatment of stroke or brain injury, chronic neurodegenerative disease such as Parkinson's disease, Alzheimer's disease, Huntington's disease or amyotrophic lateral sclerosis (ALS), epilepsy, convulsive disorder, pain, anxiety, human immunodeficiency virus (HIV) related neuronal injury, migraine, depression, schizophrenia, tumor, post-anesthesia cognitive decline (PACD), glaucoma, tinnitus, tradive dyskinesia, allergic encephalomyelitis, opioid tolerance, drug abuse, alcohol abuse, or the like in mammalian, especially humans.

The compounds of the present invention are useful for the general treatment of pain, particularly neuropathic pain. Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57: 1–164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765–1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13–44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain have both nociceptive and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13–44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertabral discs or abnormalities of the lumber facet joints, sacroiliac joints, paraspinal muscles or the posterior longitudinal ligament.

Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959–1964). The symptoms of neuropathic pain are difficult to treat, as they are often heterogeneous even between patients with the same disease (Woolf & Decosterd 1999 Pain Supp. 6: S141–S147; Woolf and Mannion 1999 Lancet 353: 1959–1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45–56). Arthritic pain makes up the majority of the inflammatory pain population. Rheumatoid disease is one of the commonest chronic inflammatory conditions in developed countries and rheumatoid arthritis is a common cause of disability. The exact aetiology of RA is unknown, but current hypotheses suggest that both genetic and microbiological factors may be important (Grennan & Jayson 1994 Textbook of Pain 397–407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36: 679–686; McCarthy et al., 1994 Textbook of Pain 387–395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD), Other types of pain include but are not limited to;

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis.

Central pain or 'thalamic pain' as defined by pain caused by lesion or dysfunction of the nervous system including but not limited to central post-stroke pain, multiple sclerosis, spinal cord injury, Parkinson's disease and epilepsy.

Heart and vascular pain including but not limited to angina, myocardical infarction, mitral stenosis, pericarditis, Raynaud's phenomenon, scleredoma, scleredoma, skeletal muscle ischemia.

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis.

Head pain including but not limited to migraine, migraine with aura, migraine without aura cluster headache, tension-type headache.

Orofacial pain including but not limited to dental pain, temporomandibular myofascial pain.

Thus, as a further aspect, the present invention provides for the use of a compound of this invention or a pharmaceutically acceptable ester of such compound, or a pharmaceutically acceptable salt thereof, as a medicament.

As a further aspect of the present invention there is provided the the use of a compound of this invention or a salt thereof in the manufacture of a medicament for the treatment of a disease caused by over activation of the NMDA NR2B receptor.

As an alternative aspect of the present invention, there is provided a method for the treatment of disease conditions caused by overactivation of NMDA NR2B receptor, in a mammalian subject, which comprises administering to said subject a therapeutically effective amount of a compound of the invention or a pharmaceutically acceptable ester of such compound, or a pharmaceutically acceptable salt thereof.

As a further or alternative aspect of the present invention there is provided the use of a compound of this invention or a salt thereof in the manufacture of a medicament for the treatment of stroke or brain injury, chronic neurodegenerative disease such as Parkinson's disease, Alzheimer's disease, Huntington's disease or amyotrophic lateral sclerosis (ALS), epilepsy, convulsive disorder, pain, anxiety, human immunodeficiency virus (HIV) related neuronal injury, migraine, depression, schizophrenia, tumor, post-anesthesia cognitive decline (PACD), glaucoma, tinnitus, tradive dyskinesia, allergic encephalomyelitis, opioid tolerance, drug abuse, alcohol abuse.

A yet further alternative aspect the present invention provides a method for the treatment of stroke or brain injury, chronic neurodegenerative disease such as Parkinson's disease, Alzheimer's disease, Huntington's disease or amyotrophic lateral sclerosis (ALS), epilepsy, convulsive disorder, pain, anxiety, human immunodeficiency virus (HIV) related neuronal injury, migraine, depression, schizophrenia, tumor, post-anesthesia cognitive decline (PACD), glaucoma, tinnitus, tradive dyskinesia, allergic encephalomyelitis, opioid tolerance, drug abuse, alcohol abuse, in a mammalian subject, which comprises administering to said subject a therapeutically effective amount of a compound of the invention or a pharmaceutically acceptable ester of such compound, or a pharmaceutically acceptable salt thereof.

Also, the present invention provides a method for the treatment of disease conditions caused by overactivation of NMDA NR2B receptor, in a mammalian subject, which comprises administering to said subject a therapeutically effective amount of a compound of formula (I).

Further, the present invention provides a method for the treatment of stroke or brain injury, chronic neurodegenerative disease such as Parkinson's disease, Alzheimer's disease, Huntington's disease or amyotrophic lateral sclerosis (ALS), epilepsy, convulsive disorder, pain, anxiety, human immunodeficiency virus (HIV) related neuronal injury, migraine, depression, schizophrenia, tumor, post-anesthesia cognitive decline (PACD), glaucoma, tinnitus, tradive dyskinesia, allergic encephalomyelitis, opioid tolerance, drug abuse, alcohol abuse, or the like in mammalian, which comprises administering to said subject a therapeutically effective amount of a compound of formula (I).

DETAILED DESCRIPTION OF THE INVENTION

General Synthesis

The 3,4-dihydroquinolin-2(1H)-one compounds of formula (I) of this invention may be prepared by a variety of synthetic methods known to those skilled in the art.

Preparation Method A

For example, the 3,4-dihydroquinolin-2(1H)-one compounds of formula (I), can be prepared by reduction of compound (II) with a suitable reducing agent as indicated in the following Scheme I:

Scheme I

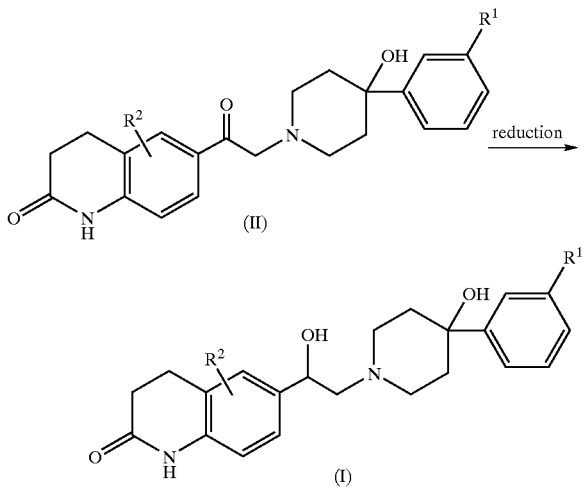

(wherein $R^1$ and $R^2$ are defined as above.)

Ketone intermediates (II) are conveniently converted to corresponding alcohols (I) by conventional reduction with a reducing agent such as, sodium borohydride(NaBH$_4$), Lithium aluminumhydride(LAH), diborane, hydrogen and a metal catalyst, zinc and hydrochoric acid, formic acid, borane dimethylsulfide complex, borane-THF, (preferably NaBH$_4$), usually in excess, in a reaction inert solvent such as methanol, ethanol, propanol, butanol, terahydrofuran (THF) (preferably methanol or ethanol), generally at temperature of −78° C. to 60° C., preferably from about 0° C. to 45° C. for 5 minutes to 24 hours, preferably 60 minutes to 12 hours.

The precursor ketones (II), can be prepared by reaction of compound (III) with compound (IV) as indicated in the following Scheme II:

Scheme II

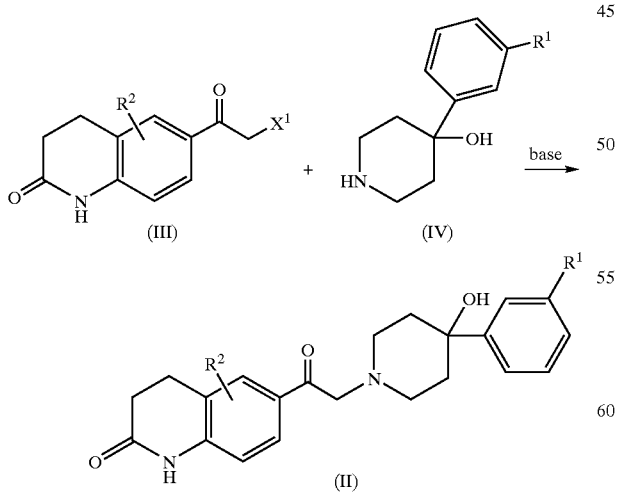

(wherein $X^1$ is halo, alkanesulfonyloxy, arylsulfonyloxy (preferably chloro or bromo); and the other symbols are as already defined)

The precursor ketones (II) are generally prepared by nucleophilic displacement of an appropriately substituted 2-halo, 2-alkanesulfonyloxy- or 2-arylsulfonyloxy-1-alkanone with an appropriately substituted piperidine derivatives (IV). This reaction is carried out under conditions typical of nucleophilic displacements in general. Where the two reactants are about equivalent in availability, substantially molar equivalents may be used; although when one is more readily available, it is usually preferred to use that one in excess, in order to force this bimolecular reaction to completion in a shorter period of time. The reaction is generally carried out in the presence of at least 1 molar equivalent of a base, the piperidine derivative itself, if it is readily available, but more usually a tertiary amine, sodium carbonate, or potassium carbonate, which is at least comparable in base strength to the mucleophilic piperidine; and in a reaction inert solvent such as methanol, ethanol, propanol, dimethylformamide (DMF), THF, (preferably ethanol, DMF). If desired, the reaction is catalyzed by the addition of up to one molar equivalent or more of an iodide salt such as NaI, KI, or quartary ammounium iodide. Temperature is not critical, but will generally be somewhat elevated in order to force the reaction to completion within a shorter time period, but not so high as to lead to undue decompositon. A temperature in the range of 0–120° C. (preferably ambient temperature—100° C.) is generally satisfactory. Conveniently, the temperature can be the reflux temperature of the reaction mixture.

The starting materials in the aforementioned general syntheses may be obtained by conventional methods known to those skilled in the art.

The compounds of formula (I), and the intermediates above-mentioned preparation methods can be isolated and purified by conventional procedures, such as recrystallization or chromatographic purification.

The compounds of the present invention may be prepared by a variety of processes well known for the preparation of compounds of this type, for example as shown in the following reaction schemes 1–5. Unless otherwise indicated $R^1$ and $R^2$ in the reaction schemes and discussion that follow are defined as above. An example of "protecting group", as used hereinafter, is a hydroxy or amino protecting group which is selected from typical hydroxy or amino protecting groups described in Protective Groups in Organic Synthesis edited by T. W. Greene et al. (John Wiley & Sons, 1991);

1)

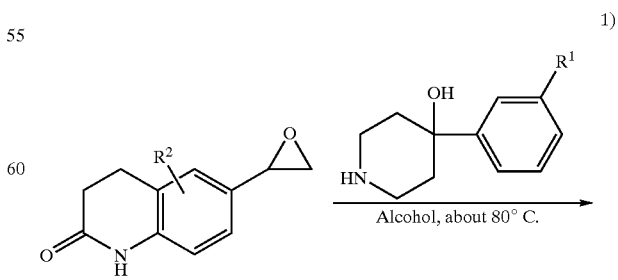

Compounds in
EP 709384

-continued
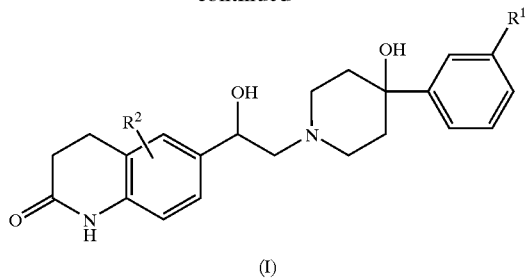
(I)
wherein the alcohol is e.g. methanol or ethanol.
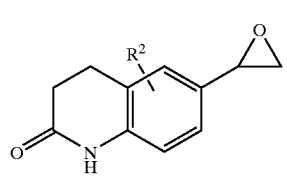
EP 709384
1)
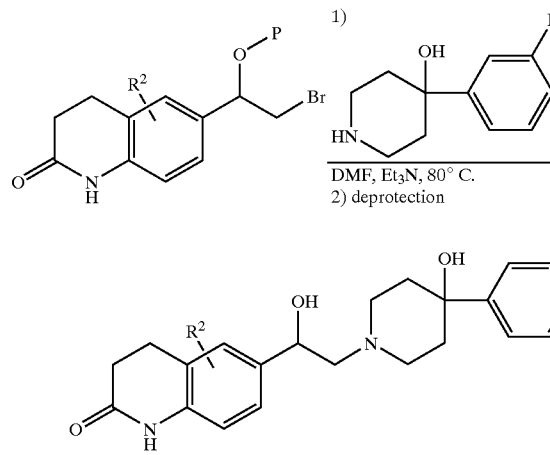
(I)
wherein P is a protection group and DMF represents N,N-dimethylformamide
3)
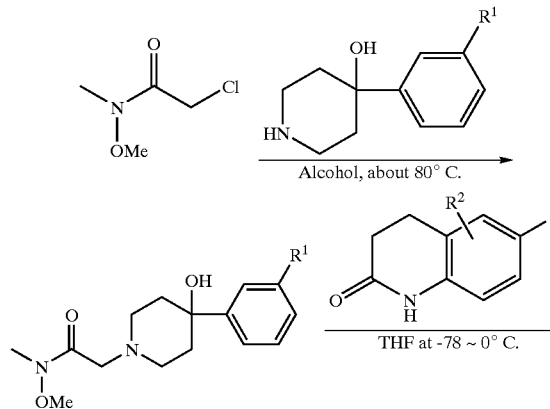
-continued
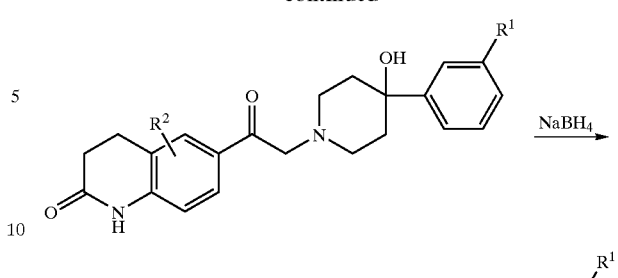
2)
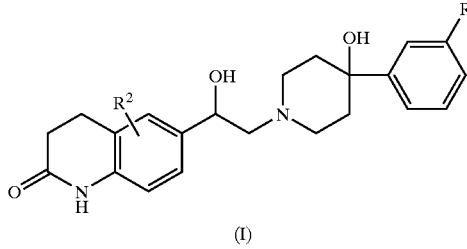
(I)
wherein the alcohol is e.g. methanol or ethanol.
4)
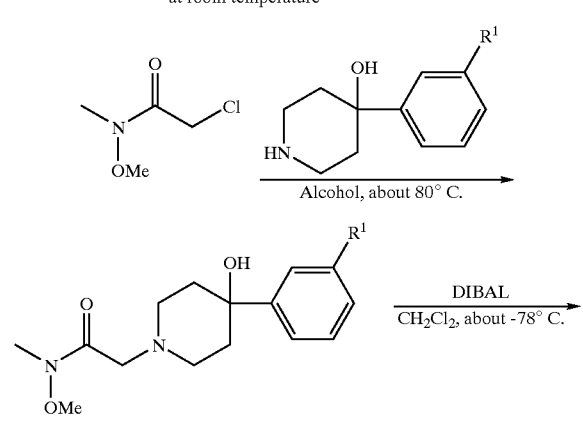
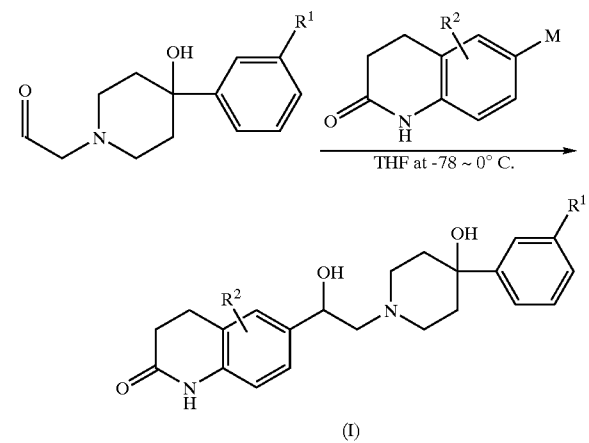
(I)
wherein DIBAL is diisopropyl azodicarboxylate; and THF is tetrahydrofuran.

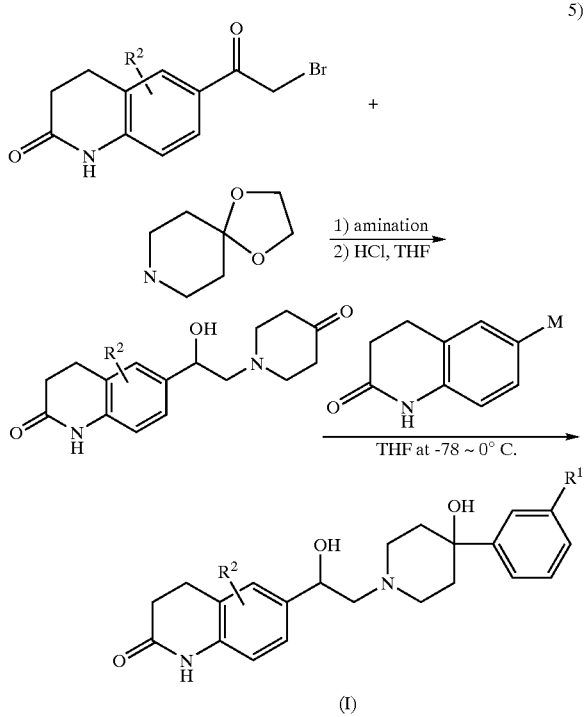

wherein THF is tetrahydrofuran.

The optically active compounds of this invention can be prepared by several methods. For example, the optically active compounds of this invention may be obtained by chromatographic separation, enzymatic resolution or fractional crystallization from the final compounds. Asymmetric reduction of the ketone (II) using chiral hydride reagents or chiral catalysts for hydrogenation may also produce optically active compounds. Optionally, a racemate of the invention may be treated with an optically active acid, e.g. mandelic acid in a suitable solvent such as acetonitrile and the resulting salt form of the enantiomers separated by chromatography.

The 3,4-dihydroquinolin-2(1H)-one compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The present invention includes salt forms of a compound of the invention as obtained above.

A compound of the invention can be converted from its free base form to a pharmaceutically acceptable salt form by conventional methods known in the art. For example, the formation of the mesylate is a typical procedure and it is carried out as follows. The free base of a compound of the invention is dissolved with methanesulfonic acid in IPA upon heating, and the solution is filtered. The filtrate was cooled and the resulting solids were collected to yield the mesylate as either crystals or a solid.

Insofar as the 3,4-dihydroquinolin-2(1H)-one compounds of this invention are basic compounds, they are capable of forming a wide variety of different salts with various inorganic and organic acids.

The acids which are used to prepare the pharmaceutically acceptable acid addition salts of the aforementioned 3,4-dihydroquinolin-2(1H)-one base compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate). The acid addition salts can be prepared by conventional procedures.

Method for Assessing Biological Activities
NR2B Binding Assay

The activity of the 3,4-dihydroquinolin-2(1H)-one compounds of the present invention, as NR2B antagonists, is determined by their ability to inhibit the binding of NR2B subunit at its receptor sites employing radioactive ligands.

The NR2B antagonist activity of the 3,4-dihydroquinolin-2(1H)-one compounds is evaluated by using the standard assay procedure described in, for example, J. Pharmacol., 331, pp117–126, 1997. This method essentially involves determining the concentration of the individual compound required to reduce the amount of radiolabelled NR2B ligands by 50% at their receptor sites, thereby affording characteristic $IC_{50}$ values for each compound tested. More specifically, the assay is carried out as follows.

Membranes were prepared by homogenization of forebrain of male CD rats weighing between 170~190 g by using glass-Teflon homogenizer in 0.32 M sucrose at 4° C. The crude nuclear pellet was removed by centrifugation at 1000×g for 10 min, and the supernatant centrifuged at 17000×g for 25 min. The resulting pellet was resuspended in 5 mM Tris acetate pH 7.4 at 4° C. for 10 min to lyse cellular particles and again centrifuged at 17000×g. The resulting pellet (P2 membrane) was washed twice in Tris acetate, resuspended at 5.5 mg protein/ml and stored at −20° C. until use. All the manipulation was done on ice, and stock solution and equipment were kept on ice at all time.

For the saturation assay, receptor saturation was determined by incubating [$^3$H]-CP-98,113 and 50 μg protein of P2 membrane for 60 minutes at room temperature in a final 100 μl of incubation buffer (50 mM Tris HCl, pH7.4). Total and non-specific bindings (in the presence of 10 μM of unlabeled CP-98,113) were determined in a range of [$^3$H]-CP-98113 concentrations (0.625 nM to 60 nM). [$^3$H]-CP-98,113 is as follows:

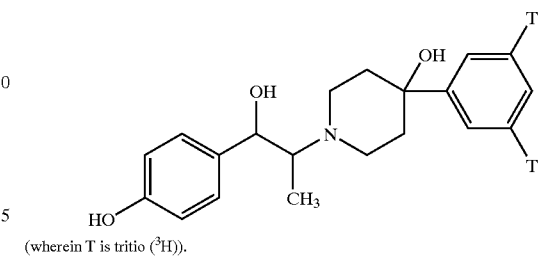

(wherein T is tritio ($^3$H)).

For the competition assay, test compounds were incubated in duplicate with 5 nM [$^3$H]-CP-98,113 and 50 μg protein of P2 membrane for 60 minutes at room temperature in a final 100 μl of 50 mM Tris HCl buffer (pH7.4). Nonspecific binding was determined by 10 μM of unlabeled CP-98,113 (25 μl). The saturation derived $K_D$ gained in saturation assay was used for all Ki calculations.

All incubations were terminated by rapid vacuum filtration over 0.2% polyethyleneimine soaked Whatman GF/B glass fibre filter paper using a SKATRON cell harvester followed by three washes with ice-cold filtration buffer (5 mM Tris HCl, pH 7.4.). Receptor-bound radioactivity was quantified by liquid scintillation counting using Packard LS counter. Competition assays were performed by counting Wallac GF/B filters on Betaplate scintillation counter (Wallac).

Dofetilide Binding Assay

Cell paste of HEK-293 cells expressing the HERG product was suspended in 10-fold volume of ice-cold wash buffer (50 mM Tris base, 10 mM KCl, 1 mM $MgCl_2$, adjusted pH 7.4). The cells were homogenized using a Polytron homogenizer and centrifuged at 48,000 g for 20 minutes at 4° C. The pellet was resuspended, homogenized and centrifuged once more in the same manner. The resultant supernatant was discarded and the final pellet was resuspended (10-fold volume of ice-cold wash buffer) and homogenized. The membrane homogenate was aliquoted and stored at -80° C. until use. All the manipulation was done on ice, and stock solution and equipment were kept on ice at all time.

For the saturation assay, experiments were conducted in a total volume of 1 ml in 48-well blocks and 200 µl in 96-well plates by Brandel and Skatron method, respectively. In Brandel method, receptor saturation was determined by incubating 100 µl of [$^3$H]-dofetilide and 750 µl of HERG homogenate (25–35 µg protein/tube) for 60 minutes at 22° C. in incubation buffer (50 mM Tris base, 10 mM KCl, 1 mM $MgCl_2$, adjusted pH 7.4). In Skatron method, it was determined by incubating 20 µl of [$^3$H]-dofetilide and 160 µl of HERG homogenate (25–35 µg protein/well) for 60 minutes at 22° C. in incubation buffer. Total and non-specific bindings (in the presence of 10 µM dofetilide) were determined in duplicate in a range of [$^3$H]-dofetilide concentrations (1 nM to 50 nM).

For the competition assay, 96-well plates were used, and a final assay volume was 200 µl. Various concentrations of test compounds were incubated in duplicate with 5 nM [$^3$H]-dofetilide (20 µl) and 25–35 µg protein of HERG homogenate (160 µl) for 90 minutes at 22° C. in the incubation buffer. Nonspecific binding was determined by 10 µM dofetilide (20 µl). The saturation derived $K_D$ gained in saturation assay was used for all Ki calculations.

All incubations were terminated by rapid vacuum filtration over 0.2% polyethyleneimine soaked glass fibre filter paper using a Brandel cell harvester followed by three washes with ice-cold filtration buffer (50 mM Tris base, 10 mM KCl, 1 mM $MgCl_2$, adjusted pH 7.4), or using Skatron harvester with the same wash buffer. Receptor-bound radioactivity was quantified by liquid scintillation counting using Packard LS counter. Competition assays were performed by counting Wallac GF/B filters on Betaplate scintillation counter (Wallac).

$I_{HERG}$ Assay

HEK 293 cells which stably express the HERG potassium channel were used for electrophysiological study. This cellline is maintained in Pfizer. Before the day of experimentation, the cells were harvested from culture flasks and plated onto glass coverslips in a standard MEM medium with 10% FCS. The plated cells were stored in an incubator at 37° C. maintained in an atmosphere of 95%$O_2$/5%$CO_2$. Cells were studied between 15–28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1–3MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15MΩ and seal resistances >1 GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient for cell dialysis with pipette solution (>5 min), a standard voltage protocol was applied to the cell to evoke-membrane currents. The voltage protocol is as follows. The membrane was depolarized from a holding potential of -80 mV to +20 mV for 1000 ms. This was followed by a descending voltage ramp (rate 0.5 mV $msec^{-1}$) back to the holding potential. The voltage protocol was applied to a cell continuously throughout the experiment every 4 seconds (0.25 Hz). The amplitude of the peak current elicited around -40 mV during the ramp was measured. Once stable evoked current responses were obtained in the external solution, vehicle (0.5% DMSO in the standard external solution) was applied for 10–20 min by a peristalic pump. Provided there were minimal changes in the amplitude of the evoked current response in the vehicle control condition, the test compound of either 0.3, 1, 3, 10 µM was applied for a 10 min period. The 10 min period includeds the time which supplying solution was passing through the tube from solution reservoir to the recording chamber via the pump. Exposing time of cells to the compound solution was more than 5 min after the drug concentration in the chamber well reached the attempting concentration. There reversibility. Finally, the cells was exposed to high dose of dofetilide (5 µM), a specific IKr blocker, to evaluate the insensitive endogenous current.

All experiments were performed at room temperature (23±1° C.). Evoked membrane currents were recorded on-line on a computer, filtered at 500–1 KHz (Bessel -3 dB) and sampled at 1–2 KHz using the patch clamp amplifier and a specific data analysing software. Peak current amplitude, which occurred at around -40 mV, was measured off line on the computer.

The arithmetic mean of the ten values of amplitude was calculated under control conditions and in the presence of drug. Percent decrease of $I_N$ in each experiment was obtained by the normalized current value using the following formula: $I_N=(1-I_D/I_C)\times 100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Test result is summarized as follows:

| Chemical Structure | NR2B Binding Ki [nM] | Dofetilide Binding Ki [μM] | TI (Dofetilide/ NR2B) | Functional Activity IC$_{50}$ [nM] |
|---|---|---|---|---|
| 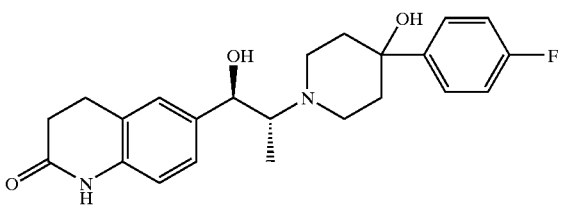 Compound A | 7.0 | 3.4 | 490 | |
| 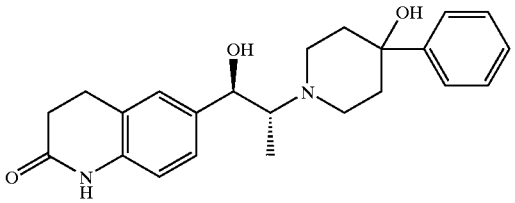 Compound B | | | | 22.4 |
| 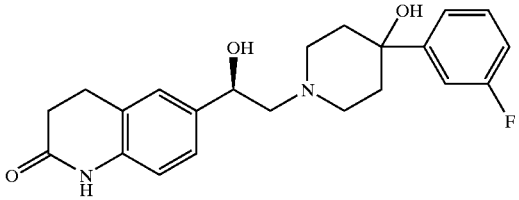 Compound of Example 1 of this invention | 3.5 | 8.3 | 2400 | 11.9 |

(wherein TI is a value of {Dofetilide Binding Ki [μM]/ NR2B Binding Ki [nM]×1000})

Furthermore, the compounds of Examples 2, 3 and 4 showed a TI value in the range of 1300–2900.

The activity of the compounds of the invention may be determined by other means, as follows:

Mice PSL Method

Surgery of partial sciatic nerve ligation (PSL) was made according to Seltzer et al. (Pain 43, 1990, 205–218). Von Fray hair test was applied slowly to the plantar surface of the hind operated paw until the hairs bent. Each hair was tested 10 times in ascending order of force to different loci of the paw with one to two second intervals between each application. Once a withdrawal response was established, the paw was re-tested with the same hair. The lowest amount of force required to elicit a response was recorded as the paw-withdrawal threshold, measured in grams.

Serum Protein Binding

Serum protein binding of NR2B topic compounds (1 uM) in humans and ddY mice were measured in method of equilibrium dialysis using 96-well plate type equipment. Spectra-Por® regenerated cellulose membranes (molecular weight cut-off 12,000–14,000, 12 mm×120 mm) was soaked for over night in distilled water, then for 20 minutes in 30% ethanol, and finally for 15 minutes in dialysis buffer (0.10 M PBS: phosphate buffered saline, pH 7.4). Fresh humans and ddY mice serum (20 ml each) was prepared. The dialysis was assembled with being careful not to puncture or tear the membranes and added 150 ul of serum to one side of each well and 150 ul of dialysis buffer to the other side of each well. After 4 hours incubation at 37° C. for 60 r.p.m, remove the serum and buffer samples and an aliquot of collected serum and buffer samples were mixed for buffer and serum at following rates:

1) 40 ul serum samples were mixed with 120 ul buffer
2) 120 ul buffer samples were mixed with 40 ul serum Then, mixed samples were extracted with 600 μl acetonitrile containing CP-96344 at 25 ng/ml (as HPLC-MS-MS internal standard) and measured in LC/MS/MS analysis.

Calculations

The fraction of substrate unbound, $f_u = 1 - \{([plasma]_{eq} - [buffer]_{eq})/([plasma]_{eq})\}$ where $[plasma]_{eq}$ and $[buffer]_{eq}$ are the concentrations of substrate in plasma and buffer, respectively.

Aqueous Solubility

Aqueous solubility in the mediums (a)–(c) was determined by method (1) or (2). (1) Vials containing approx. 1 mg of compound and 1 mL of each medium were agitated for 24 hours at room temperature. Insoluble materials were removed by centrifugation at 10,000 rpm for 10 minutes twice. The supernatants were assayed by HPLC. (2) Whatman Mini-UniPrep chambers (Clifton, N.J., USA) containing more than 0.5 mg of compound and 0.5 mL of each medium were shaken overnight (over 8 hours) at room temperature. All samples were filtered through a 0.45 μm PVDF membrane into a Whatman Mini-UniPrep plunger before analysis. The filtrates were assayed by HPLC.

<Mediums>
(a) Simulated gastric fluid with no enzyme (SGN) at pH 1.2: Dissolve 2.0 g of NaCl in 7.0 mL of 10N HCl and sufficient water to make 1000 mL.
(b) Phosphate buffered saline (PBS) at pH 6.5: Dissolve 6.35 g of $KH_2PO_4$, 2.84 g of $Na_2HPO_4$ and 5.50 g of NaCl in sufficient water to make 1000 mL, adjusting the pH of this solution to 6.5.
(c) Water for injection (WFI).

The compounds of the invention may be administered in combination, separately, simultaneously or sequentially, with one or more other pharmacologically active agents. Suitable agents, particularly for the treatment of pain, include:

(i) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(ii) nonsteroidal antiinflammatory drugs (NSAIDs), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and their pharmaceutically acceptable salts;

(iii) barbiturate sedatives, e.g. amobarbital, aprobarbital, butabarbital, butabital, mephobarbital, metharbital, methohexital, pentobarbital, phenobartital, secobarbital, talbutal, theamylal, thiopental and their pharmaceutically acceptable salts;

(iv) benzodiazepines having a sedative action, e.g. chlordiazepoxide, clorazepate, diazepam, flurazepam, lorazepam, oxazepam, temazepam, triazolam and their pharmaceutically acceptable salts, (v) $H_1$ antagonists having a sedative action, e.g. diphenhydramine, pyrilamine, promethazine, chlorpheniramine, chlorcyclizine and their pharmaceutically acceptable salts;

(vi) miscellaneous sedatives such as glutethimide, meprobamate, methaqualone, dichloralphenazone and their pharmaceutically acceptable salts;

(vii) skeletal muscle relaxants, e.g. baclofen, carisoprodol, chlorzoxazone, cyclobenzaprine, methocarbamol, orphrenadine and their pharmaceutically acceptable salts, (viii) alpha-2-delta ligands, e.g. gabapentin and pregabalin;

(ix) alpha-adrenergic active compounds, e.g. doxazosin, tamsulosin, clonidine and 4-amino-6,7-dimethoxy-2-(5-methanesulfonamido-1,2,3,4-tetrahydroisoquinol-2-yl)-5-(2-pyridyl)quinazoline;

(x) tricyclic antidepressants, e.g. desipramine, imipramine, amytriptiline and nortriptiline;

(xi) anticonvulsants, e.g. carbamazepine and valproate;

(xii) serotonin reuptake inhibitors, e.g. fluoxetine, paroxetine, citalopram and sertraline;

(xiii) mixed serotonin-noradrenaline reuptake inhibitors, e.g. milnacipran, venlafaxine and duloxetine;

(xiv) noradrenaline reuptake inhibitors, e.g. reboxetine;

(xv) Tachykinin (NK) antagonists, particularly Nk-3, NK-2 and NK-1 antagonists, e.g. (αR,9R)-7-[3,5-bis (trifluoromethyl)benzyl]-8,9,10,11-tetrahydro-9-methyl-5-(4-methylphenyl)-7H-[1,4]diazocino[2,1-g][1,7] naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl] methylamino]-2-phenyl-piperidine (2S,3S)

(xvi) Muscarinic antagonists, e.g oxybutin, tolterodine, propiverine, tropsium chloride and darifenacin;

(xvii) COX-2 inhibitors, e.g. celecoxib, rofecoxib and valdecoxib;

(xviii) Non-selective COX inhibitors (preferably with GI protection), e.g. nitroflurbiprofen (HCT-1026);

(xix) coal-tar analgesics, in particular, paracetamol;

(xx) neuroleptics, such as droperidol;

(xxi) Vanilloid receptor agonists, e.g. resinferatoxin;

(xxii) Beta-adrenergic compounds such as propranolol;

(xxiii) Local anaesthetics, such as mexiletine;

(xxiv) Corticosteriods, such as dexamethasone (xxv) serotonin receptor agonists and antagonists;

(xxvi) cholinergic (nicotinic) analgesics; and (xxvii) miscellaneous analgesic agents, such as Tramadol®.

Thus, the invention further provides a combination comprising a compound of the invention or a pharmaceutically acceptable salt, solvate or pro-drug thereof, and a compound or class of compounds selected from the group (i)–(xxvii), above. There is also provided a pharmaceutical composition composition comprising such a combination, together with a pharmaceutically acceptable excipient, diluent or carrier, particularly for the treatment of a disease for which an alpha-2-delta ligand is implicated.

Combinations of the compounds of the present invention and other therapeutic agents may be administered separately, sequentially or simultaneously. Thus, the present invention extends to a kit comprising a compound of the invention, one or more other therapeutic agents, such as those listed above, and a suitable container.

The compounds of the present invention may be formulated by any convenient means using well-known carriers and excipients. Thus, the present invention also provides a pharmaceutical composition comprising a compound of the invention or a pharmaceutically acceptable ester or a pharmaceutically acceptable salt thereof with one or more pharmaceutically acceptable carriers.

The present invention further provides a pharmaceutical composition for the treatment of disease conditions caused by overactivation of NMDA NR2B receptor, in a mammalian subject, which comprises administering to said subject a therapeutically effective amount of a compound of the invention.

Further, the present invention also provides a pharmaceutical composition for the treatment of stroke or brain injury, chronic neurodegenerative disease such as Parkinson's disease, Alzheimer's disease, Huntington's disease or amyotrophic lateral sclerosis (ALS), epilepsy, convulsive disorder, pain, anxiety, human immunodeficiency virus (HIV) related neuronal injury, migraine, depression, schizophrenia, tumor, post-anesthesia cognitive decline (PACD), glaucoma, tinnitus, tradive dyskinesia, allergic encephalomyelitis, opioid tolerance, drug abuse, alcohol abuse, or the like, which comprises a therapeutically effective amount of the 3,4-dihydroquinolin-2(1H)-one compound of the invention or its pharmaceutically acceptable salt together with a pharmaceutically acceptable carrier.

Among them, the composition is preferably for the treatment of pain, stroke, traumatic brain injury, Parkinson's disease, and Alzheimer's disease.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM) or Fuji Silysia Chromatorex® DU3050 (Amino Type, 30–50 μm). Low-resolution mass spectral data (EI) were obtained on a Automass 120 (JEOL) mass spectrometer. Low-resolution mass spectral data (ESI) were obtained on a Quattro II (Micromass) mass spectrometer. Melting point was obtained using Seiko Instruments Inc. Exstar 6000. NMR data was determined at 270 MHz (JEOL JNM-LA 270 spectrometer) or 300 MHz (JEOL JNM-LA 300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.).

Chemical symbols have their usual meanings; b.p. (boiling point), m.p. (melting point), 1 (liter(s)), ml (milliliter(s)), g (gram(s)), mg(milligram(s)), mol (moles), mmol (millimoles), eq. (equivalent(s)).

Example 1

(R)-6-[2-[4-(3-Fluorophenyl)-4-hydroxy-1-piperidinyl]-1-hydroxyethyl]-3,4-dihydroquinolin-2 (1H)-one mesylate and (S)-6-[2-[4-(3-Fluorophenyl)-4-hydroxy-1-piperidinyl]-1-hydroxyethyl]-3,4-dihydro-2(1H)-quinolinone mesylate A (i). 6-[[4-(3-Fluorophenyl)-4-hydroxy-1-piperidinyl] acetyl]-3,4-dihydroquinolin-2(1H)-one To a stirred solution of 6-(Chloroacetyl)-3,4-dihydroquinolin-2(1H)-one (WO 9302052)(8.0 g, 36 mmol) in DMF (50 ml) were added 4-(3-Fluorophenyl)-4-piperidinol (U.S. Pat. No. 4,292,321) (7.0 g, 36 mmol) and potassium carbonate (7.5 g, 54 mmol) at room temperature under nitrogen and the mixture was stirred for 5 hours at 60° C. The reaction mixture was poured into water (150 ml) and the precipitate was collected by filtration. The solid was slurried in isopropanol (100 ml) and the mixture was cooled to 0° C. The suspension was filtered to afford the titled compound as a pale yellow solid (9.1 g, 67%).

$^1$H NMR (300 MHz, DMSO-$d_6$) δ=10.43 (s, 1H), 7.89–7.85 (m, 2H), 7.40–7.25 (m, 3H), 7.06–6.92 (m, 2H), 4.97 (s, 1H), 3.77 (s, 2H), 2.96 (t, J=7.0 Hz, 2H), 2,78–2.46 (m, 6H), 2.02–1.86 (m, 2H), 1.62–1.52 (m, 2H) ppm.

A(ii). The reaction may be repeated with 6-(Chloroacetyl)-3,4-dihydroquinolin-2(1H)-one (34.1 kg) and 4-(3-Fluorophenyl)-4-piperidinol (28 kg) using sodium carbonate in water and isopropanol, to give the titled compound in a yield of 44%

B (i). (±)-6-[2-[4-(3-Fluorophenyl)-4-hydroxy-1-piperidinyl]-1-hydroxyethyl]-3,4-dihydroquinolin-2(1H)-one 6-[[4-(3-Fluorophenyl)-4-hydroxy-1-piperidinyl]acetyl]-3,4-dihydroquinolin-2(1H)-one (10.0 g, 26.1 mmol) was added portionwise to a solution of sodium borohydride (1.48 g, 39.2 mmol) in ethanol (73 ml) at room temperature, and the mixture was stirred overnight. The precipitate was collected by filtration and the resulting solid was poured into methanol (40 ml) at 0° C. The resulting suspension was filtered to afford the titled compound. (7.2 g, 72%)

$^1$H NMR (300 MHz, DMSO-$d_6$) δ=10.03 (s, 1H), 7.40–7.24 (m, 3H), 7.18–6.98 (m, 3H), 6.79 (d, J=7.9 Hz, 1H), 4.93 (s, 1H), 4.82 (s, 1H), 4.68–4.59 (m, 1H), 2.86 (t, J=7.4 Hz, 2H), 2.80–2.68 (m, 2H), 2.62–2.36 (m, 6H), 2.02–1.86 (m, 2H), 1.61–1.50 (m, 2H) ppm.

B(ii). The reaction may be repeated with 6-[[4-(3-Fluorophenyl)-4-hydroxy-1-piperidinyl]acetyl]-3,4-dihydroquinolin-2(1H)-one (25.2 kg) using sodium borohydride in tetrahydrofuran and methanol to give the titled compound, which may be isolated as its hydrochloride salt using 1N aq. HCl (91%).

C. (R)-6-[2-[4-(3-Fluorophenyl)-4-hydroxy-1-piperidinyl]-1-hydroxyethyl]-3,4-dihydroquinolin-2(1H)-one mesylate and (S)-6-[2-[4-(3-Fluorophenyl)-4-hydroxy-1-piperidinyl]-1-hydroxyethyl]-3,4-dihydro-2(1H)-quinolinone mesylate The titled enantiomers were obtained by preparative separation of the racemate, 6-[2-[4-(3-Fluorophenyl)-4-hydroxy-1-piperidinyl]-1-hydroxyethyl]-3,4-dihydroquinolin-2(1H)-one by using a chiral HPLC column (DAICEL CHIRALCEL OF, 20×250 mm, mobile phase; n-hexane/2-propanol/diethylamine=50/50/0.1).

(R)-enantiomer (free)

$^1$H NMR (300 MHz, DMSO-d$_6$) δ=10.01 (s, 1H), 7.40–7.24 (m, 3H), 7.18–6.98 (m, 3H), 6.77 (d, J=8.1 Hz, 1H), 4.91 (s, 1H), 4.81 (d, J=3.1 Hz, 1H), 4.68–4.59 (m, 1H), 2.85 (t, J=7.5 Hz, 2H), 2.80–2.68 (m, 2H), 2.62–2.36 (m, 6H), 2.02–1.86 (m, 2H), 1.61–1.50 (m, 2H) ppm.

(S)-enantiomer (free)

$^1$H NMR (300 MHz, DMSO-d$_6$) δ=10.00 (s, 1H), 7.40–7.24 (m, 3H), 7.15 (s, 1H), 7.11 (dd, J=1.8, 8.1 Hz, 1H), 7.06–6.98 (m, 1H), 6.79 (d, J=8.1 Hz, 1H), 4.92 (s, 1H), 4.82 (d, J=2.9 Hz, 1H), 4.69–4.58 (m, 1H), 2.86 (t, J=7.1 Hz, 2H), 2.80–2.68 (m, 2H), 2.65–2.35 (m, 6H), 2.04–1.84 (m, 2H), 1.62–1.50 (m, 2H) ppm.

Methanesulfonic acid (1 eq.) was added to a suspension of each enantiomer in 2-propanol to dissolve. After filtration, the filtrate was standing overnight. The solid was collected by filtration and dried in vacuum at 70° C. to afford the titled compound.

(R)-enantiomer (mesylate)

$^1$H NMR (300 MHz, DMSO-d$_6$) δ=10.14 (s, 1H), 9.23 (s, 1H), 7.49–7.40 (m, 1H), 7.32–7.18 (m, 4H), 7.15–7.07 (m, 1H), 6.87 (d, J=8.1 Hz, 1H), 6.22 (s, 1H), 5.63 (s 1H), 5.03 (d, J=10.4 Hz, 1H), 3.66–3.58 (m, 1H), 3.52–3.14 (m, 7H), 2.93–2.84 (m, 2H), 2.32 (s, 3H), 2.53–2.21, (m, 2H), 1.92–1.70 (m, 2H) ppm.

MS (ESI); M+H$^+$=385.15, M–H$^+$=383.20

IR (KBr); 3261, 3050, 2737, 1655 cm$^{-1}$ $[α]_D^{24}$=–29.46 (c=0.1154, methanol)

m.p. 180–182° C.

(S)-enantiomer (mesylate)

$^1$H NMR (300 MHz, DMSO-d$_6$) δ=10.14 (s, 1H), 9.21 (s, 1H), 7.49–7.40 (m, 1H), 7.32–7.18 (m, 4H), 7.15–7.07 (m, 1H), 6.87 (d, J=8.1 Hz, 1H), 6.21 (s, 1H), 5.63 (s 1H), 5.03 (d, J=10.4 Hz, 1H), 3.66–3.58 (m, 1H), 3.52–3.14 (m, 7H), 2.93–2.84 (m, 2H), 2.31 (s, 3H) 2.53–2.21, (m, 2H), 1.92–1.70 (m, 2H) ppm.

MS (ESI); M+H$^+$=385.10, M–H$^+$=383.17

IR (KBr); 3258, 3038, 2731, 1654 cm$^{-1}$ $[α]_D^{24}$=+38.69 (c=0.1034, methanol)

m.p. 178–179° C.

D. (R)-6-[2-[4-(3-Fluorophenyl)-4-hydroxy-1-piperidinyl]-1-hydroxyethyl]-3,4-dihydroquinolin-2(1H)-one (±)-6-[2-[4-(3-Fluorophenyl)-4-hydroxy-1-piperidinyl]-1-hydroxyethyl]-3,4-dihydroquinolin-2(1H)-one was isolated from its hydrochloride with aq. potassium carbonate to yield the free amine in a 99% yield. To a mixture of (±)-6-[2-[4-(3-Fluorophenyl)-4-hydroxy-1-piperidinyl]-1-hydroxyethyl]-3,4-dihydroquinolin-2(1H)-one (2.1 kg) and (D)-(–) madelic acid (989 g) was added actonitrile (80L) the mixture stirred at room temperature to facilitate dissolution than at 55–65° C. for 4–6 hours. The subsequent mixture was cooled then filtered, washed with acetonitrile and dried to give the mandelic acid salt (1.5 kg). The desired enantiomer was obtained by chiral chromatography of the racemic mandelic acid salt (3.82 kg) (Chiralpak AD, (20 μm particles)), eluting with acetonitrile/methanol/diethylamine (75/25/0.1) and the resulting material treated with a mixture of sodium carbonate, isopropanol, methanol and water to give the titled product (840 g).

Example 2

6-{1-Hydroxy-2-[4-hydroxy-4-(3-methoxyphenyl)-1-piperidinyl]ethyl}-3,4-dihydroquinolin-2(1H)-one Hydrochloride A. 6-{[4-Hydroxy-4-(3-methoxyphenyl)-1-piperidinyl]acetyl}-3,4-dihydroquinolin-2(1H)-one To a stirred solution of 6-(Chloroacetyl)-3,4-dihydroquinolin-2(1H)-one (7.30 g, 32.7 mmol) in DMF (32 ml) were added 4-(3-methoxyphenyl)-4-piperidinol (*J. Labelled Compd. Radiopharm.*, 41, p464, 1998). (8.12 g, 39.2 mmol) and triethylamine (13.7 ml, 98.0 mmol) at room temperature under nitrogen. The reaction mixture was stirred for 4 hours at room temperature and poured into water (80 ml). The precipitate was collected by filtration and washed with dichloromethane (20 ml). The solid was stirred in 0.5N NaOH (65 ml) for 1 hour at room temperature and the suspension was filtered to afford the title compound (5.98 g, 46%) as a yellow solid.

$^1$H NMR (300 MHz, DMSO-d$_6$) δ=10.43 (s, 1H), 7.92–7.83 (m, 2H), 7.22 (t, J=7.7 Hz, 1H), 7.07–6.98 (m, 2H), 6.93 (d, J=8.37 Hz, 1H), 6.81–6.74 (m, 1H), 4.81 (s, 1H), 3.76 (s, 2H), 3.74 (s, 3H), 3.05–2.43 (m, 8H), 2.01–1.85 (m, 2H), 1.62–1.50 (m, 2H) ppm

MS (ESI); (M+H)$^+$(395.06), (M–H)$^-$(393.13)

B. 6-{1-Hydroxy-2-[4-hydroxy-4-(3-methoxyphenyl)-1-piperidinyl]ethyl}-3,4-dihydroquinolin-2(1H)-one To a stirred solution of sodium borohydride (1.15 g, 30.3 mmol) in ethanol (100 ml) was added suspension of 6-{[4-Hydroxy-4-(3-methoxyphenyl)-1-piperidinyl]acetyl}-3,4-dihydroquinolin-2(1H)-one (5.98 g, 15.2 mmol) in ethanol (40 ml) at 0° C. and the reaction mixture was stirred at room temperature overnight. The precipitate was filtered and added to methanol (20 ml). The precipitate was collected by filtration to afford the title compound (4.13 g, 69%) as a white solid.

$^1$H NMR (300 MHz, DMSO-d$_6$) δ=10.03 (s, 1H), 7.29–7.18 (m, 1H), 7.18–7.08 (m, 2H), 7.08–6.99 (m, 2H), 6.83–6.73 (m, 2H), 4.90–4.71 (m, 2H), 4.69–4.57 (m, 1H), 3.75 (s, 3H), 2.93–2.80 (m, 2H), 2.80–2.64 (m, 2H), 2.64–2.32 (m, 6H), 2.04–1.84 (m, 2H), 1.64–1.48 (m, 2H) ppm

MS (ESI); (M+H)$^+$(397.08), (M–H)$^-$(395.15)

C. 6-{1-Hydroxy-2-[4-hydroxy-4-(3-methoxyphenyl)-1-piperidinyl]ethyl}-3,4-dihydroquinolin-2(1H)-one hydrochloride To a suspension of 6-{1-Hydroxy-2-[4-hydroxy-4-(3-methoxyphenyl)-1-piperidinyl]ethyl}-3,4-dihydroquinolin-2(1H)-one (1.10 g, 2.77 mmol) in methanol (11 ml) was added 4N HCl-ethylacetate (0.76 ml, 3.05 mmol) at 0° C. and the reaction mixture was stirred at room temperature for 4 hours. The mixture was diluted with methanol (20 ml) and filtered. The filtrate was concentrated in vacuo and the obtained solid was recrystallized from 2-propanol to afford the title compound (1.10 g, 92%) as a white solid.

$^1$H NMR (300 MHz, DMSO-d$_6$) δ=10.20–10.01 (m, 2H), 7.36–7.16 (m, 3H), 7.13–6.97 (m, 2H), 6.91–6.76 (m, 2H), 6.17 (brs, 1H), 5.50 (s, 1H), 5.18–4.99 (m, 1H), 3.77 (s, 3H), 3.67–3.10 (m, 5H), 2.95–2.80 (m, 2H), 2.59–2.27 (m, 5H), 1.87–1.66 (m, 2H) ppm

MS (ESI); (M+H)$^+$(397.07), (M–H)$^-$(395.14)

IR (KBr) 3327, 2964, 2740, 1688, 1670, 1603, 1508, 1433, 1377, 1259, 1175, 1138, 1038, 978, 835, 783, 700 cm$^{-1}$ m.p. 246.9° C.

Example 3

5-Fluoro-6-{1-hydroxy-2-[4-hydroxy-4-(3-methoxyphenyl)-1-piperidinyl]ethyl}-3,4-dihydroquinolin-2(1H)-one hydrochloride A. Diethyl 2-(2-fluoro-6-nitrobenzyl)malonate To a suspension of NaH (5.2 g, 130 mmol) in DMF/THF (110 ml/45 ml) was added diethyl malonate (19 ml, 125 mmol) dropwise and the mixture was stirred for 30 min at room temperature. To the mixture was added 2-(Bromomethyl)-1-fluoro-3-nitrobenzene (29 g, 124 mmol)

in DMF/THF (40 ml/30 ml) and the resulting mixture was refluxed for 3 h. After cooling, the excess reagent was quenched with brine and the mixture was extracted with ethyl acetate. The extract was dried over sodium sulfate and concentrated in vacuo to afford diethyl 2-(2-Fluoro-6-nitrobenzyl)malonate (48 g) as a brown oil. This crude product was used in the next step without further purification.

$^1$H NMR (300 MHz, CDCl$_3$) δ=7.77 (d, J=8.1 Hz, 1H), 7.50–7.24 (m, 2H), 4.18 (q, J=7.1 Hz, 4H), 3.76 (t, J=7.7 Hz, 1H), 3.55 (dd, J=7.7, 1.6 Hz, 2H), 1.23 (t, J=7.1 Hz, 6H) ppm B. 3-(2-Fluoro-6-nitrophenyl)propanoic acid The mixture of Diethyl 2-(2-fluoro-6-nitrobenzyl)malonate (crude 48 g) and 6N HCl aq. (100 ml) in acetic acid (100 ml) was refluxed for 7 h. After evaporating solvent, the resulting solid was collected and triturated with water to afford a mixture of 3-(2-Fluoro-6-nitrophenyl)propanoic acid and Ethyl 3-(2-fluoro-6-nitrophenyl)propanoate (18 g). The mixture (18 g) and 2N NaOH aq. (450 ml) in ethanol (450 ml) were refluxed for 1 h. After cooling, the mixture was acidified with 2N HCl aq. and extracted with dichloromethane. The extract was dried over sodium sulfate and concentrated in vacuo to afford 3-(2-Fluoro-6-nitrophenyl)propanoic acid (15 g) as a brown solid. This crude product was used in the next step without further purification.

$^1$H NMR (300 MHz, d-DMSO) δ=7.82 (d, J=7.9 Hz, 1H), 7.66–7.50 (m, 2H), 3.03 (t, J=7.5 Hz, 2H), 2.54 (t, J=7.5 Hz, 2H)

C. 5-Fluoro-3,4-dihydroquinolin-2(1H)-one

The suspension of 3-(2-fluoro-6-nitrophenyl)propanoic acid (6.0 g, 28 mmol) and 10% Pd-C (300 mg) in MeOH was hydrogenated under H$_2$ (4 atm) for 3 h. After filtration, the filtrate was concentrated in vacuo to afford 5-Fluoro-3,4-dihydroquinolin-2(1H)-one (4.6 g) as a slightly brown solid. This crude product was used in the next step without further purification.

$^1$H NMR (300 MHz, DMSO-d$_6$) δ=10.2 (s, 1H), 7.16 (dd, J=14.5, 8.2 Hz, 1H), 6.77 (d, J=8.4 Hz, 1H), 6.69 (d, J=8.1 Hz, 1H), 2.87 (t, J=7.5 Hz, 2H), 2.47 (t, J=7.3 Hz, 2H) ppm D. 6-(Bromoacetyl)-5-fluoro-3,4-dihydroquinolin-2(1H)-one To a stirring suspension of aluminum chloride (8.0 g, 60 mmol) in 1,2-dichloroethane (16 ml) was added bromoacetyl bromide (4.2 ml, 48 mmol) at 0° C. After 30 min, to a suspension was added 5-Fluoro-3,4-dihydroquinolin-2(1H)-one (4.0 g, 24 mmol) portionwise, then the mixture was allowed to warm to 50° C. and stirred for 4 h. After cooling, the solvent was evaporated in vacuo and the residue was quenched with ice-water and extracted with ethyl acetate. The extract was dried over sodium sulfate and concentrated in vacuo. The residue was purified by column chromatography (hexane/ethyl acetate=1/1) to afford 6-(Bromoacetyl)-5-fluoro-3,4-dihydroquinolin-2(1H)-one (2.0 g) as a yellow solid.

$^1$H NMR (300 MHz, DMSO-d$_6$) δ=10.7 (s, 1H), 7.75 (t, J=8.3 Hz, 1H), 7.49 (d, J=8.4 Hz, 1H), 4.74 (d, J=2.4 Hz, 2H), 2.95 (t, J=7.9 Hz, 2H), 2.54 (t, J=8.1 Hz, 2H) ppm E. 5-Fluoro-6-[[4-hydroxy-4-(3-methoxyphenyl)-1-piperidinyl]acetyl]-3,4-dihydroquinolin-2(1H)-one To a cooled solution of 6-(Bromoacetyl)-5-fluoro-3,4-dihydro-2(1H)-quinolinone (900 mg, 3.1 mmol) and triethylamine (0.88 ml, 6.3 mmol) in DMF (15 ml) was added dropwise a solution of 4-(3-Methoxyphenyl)-4-piperidinol (650 mg, 3.1 mmol) in DMF(15 ml) at 0° C. The mixture was stirred at room temperature for 3 h. The reaction mixture was added water and the resulting precipitate was filtered to afford 5-Fluoro-6-[[4-hydroxy-4-(3-methoxyphenyl)-1-piperidinyl]acetyl]-3,4-dihydroquinolin-2(1H)-one (360 mg) as a brown solid. The filtrate was extracted with ethyl acetate. The extract was dried over sodium sulfate and concentrated in vacuo. The residue was purified by column chromatography (dichloromethane/methanol=20/1) to afford 5-Fluoro-6-[[4-hydroxy-4-(3-methoxyphenyl)-1-piperidinyl]acetyl]-3,4-dihydroquinolin-2(1H)-one as a yellow solid (270 mg). The obtained products were combined and used in the next step without further purification.

F. 5-Fluoro-6-[1-hydroxy-2-[4-hydroxy-4-(3-methoxyphenyl)-1-piperidinyl]ethyl]-3,4-dihydroquinolin-2(1H)-one The mixture of 5-Fluoro-6-[[4-hydroxy-4-(3-methoxyphenyl)-1-piperidinyl]acetyl]-3,4-dihydroquinolin-2(1H)-one (630 mg, 1.5 mmol) and sodium borohydride (57 mg, 1.5 mmol) in ethanol (17 ml) was stirred at room temperature overnight. To the mixture was added water and extracted with dichloromethane. The extract was dried over sodium sulfate and concentrated in vacuo. The residue was purified by column chromatography (dichloromethane/methanol=10/1) to afford 5-Fluoro-6-[1-hydroxy-2-[4-hydroxy-4-(3-methoxyphenyl)-1-piperidinyl]ethyl]-3,4-dihydroquinolin-2(1H)-one as a yellow solid (220 mg).

$^1$H NMR (300 MHz, DMSO-d$_6$) δ=10.2 (s, 1H), 7.30–7.20 (m, 2H), 7.05–7.00 (m, 2H), 6.80–6.74 (m, 2H), 6.68 (d, J=8.2 Hz, 1H), 5.10–4.90 (br, 2H), 4.78(s, 1H), 3.74 (s, 3H), 2.87 (t, J=7.3 Hz, 2H), 2.80–2.65 (br, 2H), 2.64–2.40 (br, 6H), 2.00–1.80(br, 2H), 1.60–1.50 (br, 2H) ppm G. 5-Fluoro-6-[1-hydroxy-2-[4-hydroxy-4-(3-methoxyphenyl)-1-piperidinyl]ethyl]-3,4-dihydroquinolin-2(1H)-one hydrochloride To a suspension of 5-Fluoro-6-[1-hydroxy-2-[4-hydroxy-4-(3-methoxyphenyl)-1-piperidinyl]ethyl]-3,4-dihydroquinolin-2(1H)-one (216 mg, 0.522 mmol) in methanol (5 ml) was added 4N HCl-AcOEt (137 μl, 0.548 mmol) and the mixture was concentrated in vacuo. The residue was crystallized twice from 2-propanol to afford 5-Fluoro-6-[1-hydroxy-2-[4-hydroxy-4-(3-methoxyphenyl)-1-piperidinyl]ethyl]-3,4-dihydroquinolin-2(1H)-one hydrochloride as a white solid (190 mg, 81%).

$^1$H-NMR (DMSO d$_6$) δ=10.3 (s, 1H), 9.85–9.65 (br, 1H), 7.40–7.25 (m, 2H), 7.10–7.00 (m, 2H), 6.88–6.80 (m, 1H), 6.75 (d, J=8.1 Hz, 1H), 6.28 (d, J=4.0 Hz, 1H), 5.48 (s, 1H), 5.40–5.25 (m, 1H), 3.77 (s, 3H), 3.80–3.45 (m, 2H), 3.40–3.10 (m, 4H), 2.90 (t, J=7.7 Hz, 2H), 2.65–2.20 (m, 4H), 1.90–1.65 (m, 2H) ppm

MS (ESI) 415 (M+H)$^+$, 413 (M–H)$^-$

IR (KBr) 3339, 3211, 2945, 1697, 1636, 1603, 1379, 1261, 1041, 829, 783, 698 cm$^{-1}$

Example 4

6-[1-Hydroxy-2-[4-hydroxy-4-(3-methylphenyl)piperidin-1-yl]ethyl]-3,4-dihydroquinolin-2(1H)-one mesylate A. 6-[[4-Hydroxy-4-(3-methylphenyl)piperidin-1-yl]acetyl]-3,4-dihydroquinolin-2(1H)-one This compound was prepared by a procedure similar to that described in example 1-A as a white solid. 4-Hydroxy-4-(3-methylphenyl)piperidine was prepared according to the literature (WO-9738665).

$^1$H-NMR (DMSO-d$_6$) δ=10.42 (s, 1H), 7.90–7.82 (m, 2H), 7.32–7.15 (m, 3H), 7.04–6.91 (m, 2H), 4.75 (s, 1H), 3.75 (s, 2H), 3.00–2.91 (m, 2H), 2.75–2.45 (m, 6H), 2.30 (s, 3H), 1.99–1.86 (m, 2H), 1.62–1.50 (m, 2H) ppm.

B. 6-[1-Hydroxy-2-[4-hydroxy-4-(3-methylphenyl)piperidin-1-yl]ethyl]-3,4-dihydroquinolin-2(1H)-one This compound was prepared by a procedure similar to that described in example 1-B as a white solid.

$^1$H-NMR (DMSO-d$_6$) δ=10.00 (s, 1H), 7.30–6.96 (m, 6H), 6.80–6.74 (m, 1H), 4.79 (s, 1H), 4.69 (s, 1H), 4.66–4.57 (m, 1H), 2.89–2.33 (m, 8H), 2.28 (s, 3H), 1.99–1.82 (m, 2H), 1.58–1.47 (m, 2H) ppm.

C. 6-[1-Hydroxy-2-[4-hydroxy-4-(3-methylphenyl)piperidin-1-yl]ethyl]-3,4-dihydroquinolin-2(1H)-one mesylate This compound was prepared by a procedure similar to that described in example 2-C as a white solid.

$^1$H-NMR (DMSO-d$_6$) δ=10.11 (s, 1H), 9.18 (s, 1H), 7.30–7.02 (m, 6H), 6.84 (d, J=8.1 Hz, 1H), 6.17 (d, J=3.3 Hz, 1H), 5.05 (m, 1H), 3.64–3.15 (m, 6H), 2.91–2.83 (m, 2H), 2.50–2.18 (m, 8H), 1.88–1.67 (m, 2H) ppm.

IR; 3236, 1668, 1375, 1198, 1045, 785

Mass (ESI); (M+H)$^+$381.16, (M–H)$^-$379.27 m.p. 98–100° C. (decomposed)

The chemical structures of the compounds prepared in the Examples 1 to 4 are summarized in the following table.

TABLE

| Ex. # | R$^1$ | R$^2$ |
|---|---|---|
| 1 | fluoro | hydrogen |
| 2 | methoxy | hydrogen |
| 3 | methoxy | fluoro |
| 4 | methyl | hydrogen |

Pharmaceutical Composition Examples

In the following Examples, the term 'active compound' or 'active ingredient' refers to a compound of formula (I) or a pharmaceutically acceptable salt, solvate or pro-drug thereof, according to the present invention.

(i) Tablet Compositions

The following compositions A and B can be prepared by wet granulation of ingredients (a) to (c) and (a) to (d) with a solution of povidone, followed by addition of the magnesium stearate and compression.

| Composition A | mg/tablet | mg/tablet |
|---|---|---|
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
| | 500 | 300 |
| Composition B | mg/tablet | mg/tablet |
| (a) Active ingredient | 250 | 250 |
| (b) Lactose | 150 | 150 |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
| | 500 | 300 |
| Composition C | mg/tablet | |
| Active ingredient | 100 | |
| Lactose | 200 | |
| Starch | 50 | |
| Povidone | 5 | |
| Magnesium Stearate | 4 | |
| | 359 | |

The following compositions D and E can be prepared by direct compression of the admixed ingredients. The lactose used in formulation E is of the direct compression type.

| | mg/tablet |
|---|---|
| Composition D | |
| Active ingredient | 250 |
| Magnesium Stearate | 4 |
| Pregelatinised Starch NF15 | 146 |
| | 400 |
| Composition E | |
| Active ingredient | 250 |
| Magnesium Stearate | 5 |
| Lactose | 145 |
| Avicel | 100 |
| | 500 |
| Composition F (Controlled release composition) | |
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

The composition can be prepared by wet granulation of ingredients (a) to (c) with a solution of povidone, followed by addition of the magnesium stearate and compression.

Composition G (Enteric-Coated Tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-Coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudgragit L). Except for Eudgragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions

Composition A

Capsules can be prepared by admixing the ingredients of Composition D above and filling two-part hard gelatin capsules with the resulting mixture. Composition B (infra) may be prepared in a similar manner.

|  | mg/capsule |
| --- | --- |
| Composition B | |
| (a) Active ingredient | 250 |
| (b) Lactose B.P. | 143 |
| (c) Sodium Starch Glycollate | 25 |
| (d) Magnesium Stearate | 2 |
|  | 420 |
| Composition C | |
| (a) Active ingredient | 250 |
| (b) Macrogol 4000 BP | 350 |
|  | 600 |

Capsules can be prepared by melting the Macrogol 4000 BP, dispersing the active ingredient in the melt and filling two-part hard gelatin capsules therewith.

| Composition D | mg/capsule |
| --- | --- |
| Active ingredient | 250 |
| Lecithin | 100 |
| Arachis Oil | 100 |
|  | 450 |

Capsules can be prepared by dispersing the active ingredient in the lecithin and arachis oil and filling soft, elastic gelatin capsules with the dispersion.

| Composition E (Controlled release capsule) | mg/capsule |
| --- | --- |
| (a) Active ingredient | 250 |
| (b) Microcrystalline Cellulose | 125 |
| (c) Lactose BP | 125 |
| (d) Ethyl Cellulose | 13 |
|  | 513 |

The controlled release capsule formulation can be prepared by extruding mixed ingredients (a) to (c) using an extruder, then spheronising and drying the extrudate. The dried pellets are coated with a release controlling membrane (d) and filled into two-part, hard gelatin capsules.

| Composition F (Enteric capsule) | mg/capsule |
| --- | --- |
| (a) Active ingredient | 250 |
| (b) Microcrystalline Cellulose | 125 |
| (c) Lactose BP | 125 |

-continued

| Composition F (Enteric capsule) | mg/capsule |
| --- | --- |
| (d) Cellulose Acetate Phthalate | 50 |
| (e) Diethyl Phthalat | 5 |
|  | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-Coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) or a plasticizer to prevent membrane cracking during application or on storage. Suitable plasticizers include diethyl phthalate, tributyl citrate and triacetin.

| (iii) Intravenous injection composition | |
| --- | --- |
| Active ingredient | 0.200 g |
| Sterile, pyrogen-free phosphate buffer (pH 9.0) to | 10 ml |

The active ingredient is dissolved in most of the phosphate buffer at 35–40° C., then made up to volume and filtered through a sterile micropore filter into sterile 10 ml glass vials (Type 1) which are sealed with sterile closures and overseals.

| (iv) Intramuscular injection composition | |
| --- | --- |
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup composition | |
| --- | --- |
| Active ingredient | 0.25 g |
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (vi) Suppository composition | mg/suppositor |
|---|---|
| Active ingredient | 250 |
| Hard Fat, BP (Witepsol H15 - Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

| (vii) Pessary composition | mg/pessary |
|---|---|
| Active ingredient (631 m) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

| (viii) Transdermal composition | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm$^2$.

Throughout this application, various publications are referenced by citation or number. The disclosures of these publications in their entireties are hereby incorporated by reference into this application.

What is claimed is:

1. A compound which is (R)-6-[2-[4-(3-fluorophenyl)-4-hydroxy-1-piperidinyl]-1-hydroxyethyl]-3,4-dihydro-2(1H)-quinolinone or a pharmaceutically acceptable ester of such compound, or a pharmaceutically acceptable salt thereof.

2. A pharmaceutical composition comprising a compound according to claim 1 or a pharmaceutically acceptable ester of such compound or a pharmaceutically acceptable salt thereof with a pharmaceutically acceptable excipient, diluent or carrier.

3. A pharmaceutical composition for the treatment of disease conditions caused by overactivation of NMDA NR2B receptor, in a mammalian subject, which comprises a therapeutically effective amount of the compound according to claim 1 or a pharmaceutically acceptable ester of such compound, or a pharmaceutically acceptable salt thereof.

4. A method for the treatment of disease conditions caused by overactivation of NMDA NR2B receptor, in a mammalian subject, which comprises administering to said subject a therapeutically effective amount of a compound according to claim 1 or a pharmaceutically acceptable ester of such compound, or a pharmaceutically acceptable salt thereof.

5. A method according to claim 4 where the disease condition is stroke or brain injury, chronic neurodegenerative disease such as Parkinson's disease, Alzheimer's disease, Huntington's disease or amyotrophic lateral sclerosis (ALS), epilepsy, convulsive disorder, pain, anxiety, human immunodeficiency virus (HIV) related neuronal injury, migraine, depression, schizophrenia, tardive dyskinesia, allergic encephalomyelitis, opioid tolerance, drug abuse or alcohol abuse.

6. A method according to claim 5 for the treatment of pain, stroke, traumatic brain injury, Parkinson's disease, Alzheimer's disease, depression, anxiety, or migraine.

* * * * *